United States Patent [19]
Tsuchida et al.

[11] Patent Number: 5,188,949
[45] Date of Patent: Feb. 23, 1993

[54] METHOD FOR PRODUCING L-THREONINE BY FERMENTATION

[75] Inventors: Takayasu Tsuchida; Naoki Katsurada; Noboru Ohtsuka; Haruo Uchibori; Takeshi Suzuki, all of Kawasaki, Japan

[73] Assignee: Ajinomoto Co., Inc., Tokyo, Japan

[21] Appl. No.: 571,821

[22] Filed: Aug. 22, 1990

Related U.S. Application Data

[63] Continuation of Ser. No. 94,897, Sep. 10, 1987, abandoned.

[30] Foreign Application Priority Data

Sep. 29, 1986 [JP] Japan .................... 61-230977
Nov. 14, 1986 [JP] Japan .................... 61-271286

[51] Int. Cl.$^5$ ............... C12P 13/08; C12N 15/00; C12N 1/20
[52] U.S. Cl. ................. 435/115; 435/172.1; 435/252.1; 435/840; 435/843
[58] Field of Search .............. 435/115, 172.1, 840, 435/843, 822, 252.1

[56] References Cited

U.S. PATENT DOCUMENTS 3,622,453  11/1971  Akeyama ................ 435/849

OTHER PUBLICATIONS

Biotechnology of Amino Acid Production, vol. 24, "Progress in Industrial Microbiology", 1986, pp. 173–182, Elsevier, Amsterdam N.; S. Nakamori: "Threonine and Homoserine".
Lynn et al., In "Amino Acids; Biosynthetic and Genetic Regulation", Addison-Wesley, 1983, pp. 173–179.
Goodfellow et al., "The Biology of Actinomycetes", Academic Press, 1984, pp. 77–79.

*Primary Examiner*—Irene Marx
*Attorney, Agent, or Firm*—Oblon, Spivak, McClelland, Maier & Neustadt

[57] ABSTRACT

A method for producing L-threonine by fermentation which comprises culturing in a culture medium a microorganism of the genus Brevibacterium or Corynebacterium which is resistant to mycophenolic acid and is capable of producing L-threonine, accumulating L-threonine in the medium, and then recovering the L-threonine accumulated therein.

1 Claim, No Drawings

METHOD FOR PRODUCING L-THREONINE BY FERMENTATION

This application is a continuation of application Ser. No. 07/094,897, filed on Sep. 10, 1987, now abandoned.

BACKGROUND OF THE INVENTION

1. Field of the Invention

The present invention relates to a method for producing L-threonine by means of fermentation.

2. Description of the Related Art

Various methods have been devised for producing L-threonine, including a method in which a mutant belonging to the genus Brevibacterium or Corynebacterium which is resistant to α-amino-β-hydroxyvaleric acid (AHV) is used (see Japanese patent publication No. 26,708/70).

In the known methods for producing L-threonine by fermentation, the yield of L-threonine is not satisfactorily high. There is therefore a continuing need to improve the yield of L-threonine in its commercial production.

SUMMARY OF THE INVENTION

Accordingly, it is an object of the present invention to provide a method for producing L-threonine by fermentation which produces a high yield of the L-threonine.

According to the present invention, the foregoing and other objects have been attained by discovering strains of the genus Brevibacterium and Corynebacterium which produce L-threonine in high yield, particularly strains which have been rendered resistant to mycophenolic acid (hereinafter referred to as "MPA"). These strains have been found to be capable of producing L-threonine in a yield which is higher than previously known L-threonine-producing microorganisms.

DETAILED DESCRIPTION OF THE PREFERRED EMBODIMENTS

According to the present invention, there can be used any microorganisms belonging to the genus Brevibacterium or Corynebacterium which are resistant to MPA and capable of producing L-threonine, including mutants derived by means of mutation with chemical mutagens or by means of X-ray or UV-ray treatments, as well as recombinants derived by means of cell fusion, recombination, or the like.

Mutants according to the present invention can be obtained by imparting the ability of producing L-threonine to wild-type strains as set forth below and then providing them with the resistance to MPA. It is also possible to obtain L-threonine producing strains which have the ability to produce L-threonine and, at the same time, are resistant to MPA by inducing resistance to MPA from an MPA-resistant L-threonine producing microorganism.

In many cases, the yield of L-threonine can be further improved if the mutant used is an auxotrophic mutant requiring isoleucine, methionine, alanine, diaminopimelic acid, lysine, leucine or the like.

Typical examples of wild strains from which the microorganisms according to the present invention can be derived include the following:

| | |
|---|---|
| *Brevibacterium lactofermentum* | ATCC 13869 |
| *Brevibacterium divaricatum* | ATCC 14020 |
| *Brevibacterium flavum* | ATCC 14067 |
| *Corynebacterium glutamicum* | ATCC 13032 |
| *Corynebacterium acetoacidophilum* | ATCC 13870 |

The full chemical name of mycophenolic acid is (E)-6-(1,3-Dihydro-4-hydroxy-6-methoxy-7-methyl-3-oxo-5-isobenzofuranyl)-4-methyl-4-hexenoic acid; 6-(4-hydroxy-6-methoxy-7-methyl-3-oxo-5-phthalanyl)-4-methyl-4-hexenoic acid. Its structure is as follows:

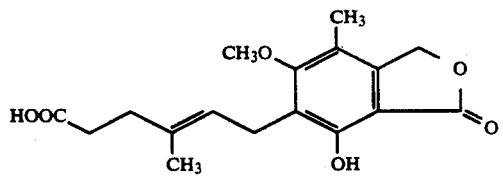

Further information on this compound may be found in the Merck Index, Ninth Edition (1976), pages 820–821.

The methods for the induction of mutation and their relation with the resistance to MPA are described hereinbelow.

Method for Inducing Mutation

Cells of *Brevibacterium flavum* ATCC 21269 (AHV-resistant strain derived from ATCC 14067) and *Corynebacterium acetoacidophilum* AJ 12315 (AHV-resistant strain derived from ATCC 13870), cultured on a bouillon agar slant at 30° C. for 24 hours, were suspended in M/30 phosphate buffer to give suspensions containing $10^9$/ml of cells. To the suspensions was added 250 μg/ml of N-methyl-N'-nitro-N-nitrosoguanidine and then the mixture was allowed to stand at 30° C. for 15 minutes. Thereafter, the cells were washed with the same buffer by means of centrifugation.

The thus obtained strains were inoculated in the medium set forth below and cultured at 31° C. for 5 hours.

| Composition of Culture Medium (pH 7.0) | |
|---|---|
| Ingredients | Contents |
| Glucose | 1.0 g/dl |
| Urea | 0.2 g/dl |
| KH$_2$PO$_4$ | 0.1 g/dl |
| MgSO$_4$.7H$_2$O | 0.1 g/dl |
| FeSO$_4$.7H$_2$O | 0.002 g/dl |
| MnSO$_4$.7H$_2$O | 0.002 g/dl |
| Biotin | 100 μg/l |
| Thiamine hydrochloride | 100 μg/l |
| MPA | 0.2 g/dl |
| Agar | 2.0 g/dl |

*Brevibacterium flavum* AJ 12312 [FERM BP-1173] (resistant to AHV and MPA) and *Corynebacterium acetoacidophilum* AJ 12316 (resistant to AHV and MPA) were obtained by selecting strains having a high L-threonine productivity from the strains growing on the above agar medium.

To the above culture medium was additionally added 15 mg/dl of L-isoleucine, and *Brevibacterium flavum* AJ 12313 (AHV-resistant, isoleucine-requiring strain derived from ATCC 14067) and *Corynebacterium acetoacidophilum* AJ 12317 (AHV-resistant, isoleucine-requiring strain derived from ATCC 13870) were cultured in the medium to effect a similar mutation as above.

*Brevibacterium flavum* AJ 12314 (resistant to AHV and MPA, and requiring isoleucine) and *Corynebacterium acetoacidophilum* AJ 12318 [FERM BP-1172] (resistant to AHV and MPA, and requiring isoleucine) were derived therefrom by selecting strains having higher L-threonine productivity.

Resistance to MPA of the thus obtained mutants was compared with that of the parent strains in the following manner.

Cells of a strain cultured on a bouillon slant for 24 hours were suspended in sterilized water, and the suspension was inoculated in a medium adjusted to a pH of 7.0 and containing 0.5 g/dl of glucose, 0.2 g/dl of urea, 0.15 g/dl of ammonium sulfate, 0.3 g/dl of $KH_2PO_4$, 0.1 g/dl of $K_2HPO_4$, 0.01 g/dl of $MgSO_4.7H_2O$, 0.01 mg/dl of $CaCl_2.2H_2O$, 100 µg/l of biotin, 100 µg/l of thiamine hydrochloride, 0.002 g/dl of $FeSO_4.7H_2O$, 0.002 g/dl of $MnSO_4.7H_2O$, 15 mg/dl of L-isoleucine (in the case of a mutant requiring isoleucine), and MPA in an amount shown in the table. After 24 hours of cultivation, the growth of the strain was determined in terms of turbidity.

TABLE 1

| Strain | Concentration of MPA (%) | | | | |
|---|---|---|---|---|---|
| | 0 | 0.005 | 0.01 | 0.05 | 0.1 |
| *Brevibacterium flavum* ATCC 21269 | 100 | 70 | 20 | 0 | 0 |
| *Brevibacterium flavum* AJ 12312 FERM BP-1173 | 100 | 100 | 82 | 5 | 0 |
| *Brevibacterium flavum* AJ 12313 | 100 | 90 | 30 | 0 | 0 |
| *Brevibacterium flavum* AJ 12314 | 100 | 100 | 100 | 20 | 5 |
| *Corynebacterium acetoacidophilum* AJ 12315 | 100 | 60 | 10 | 0 | 0 |
| *Corynebacterium acetoacidophilum* AJ 12316 | 100 | 100 | 85 | 10 | 0 |
| *Corynebacterium acetoacidophilum* AJ 12317 | 100 | 90 | 20 | 0 | 0 |
| *Corynebacterium acetoacidophilum* AJ 12318 FERM BP-1172 | 100 | 100 | 100 | 40 | 8 |

In many cases, further improved yields can be attained by imparting to the above mutants such characteristics as resistance to O-methylthreonine, resistance to D-threonine, resistant to β-hydroxyleucine and resistance to vitamin P, which characteristics are known to be generally effective for the further enhancement of the productivity of L-threonine.

Culture media to be used for the culturing of such mutants can be any ordinary media containing carbon sources, nitrogen sources, inorganic ions, substances necessary to satisfy the above-mentioned requirements and, where necessary, other organic micronutrients, such as vitamins, etc. Hydrocarbons, such as glucose and sucrose, and organic acids, such as acetic acid, etc. can be preferably used as carbon sources. Examples of preferable nitrogen sources include aqueous ammonia, ammonia gas, ammonium salts, and the like. Inorganic salts, such as potassium and magnesium ions, as well as phosphates, are added to the medium, as needed.

The cultivation is preferably carried out under aerobic conditions. Preferable results can be attained when their culturing is effected at a temperature of from 8° to 25° C., while maintaining the culture medium at a pH of from 4 to 8. After 1 to 7 days of cultivation, a substantial amount of L-threonine is accumulated, and L-lysine is formed therein in only a very small quantity. L-Threonine can be recovered from the culture medium by conventional methods, e.g., by use of ion exchange resins.

The mutants, BP-1172 and BP-1173, which were obtained as part of this invention were deposited under the Budapest Treaty on Sep. 22, 1986 at the Fermentation Research Institute, Agency of Industrial Sciences and Technology, Ministry of International Trade and Industry (FRI), 1-3, Higashi 1-Chome, Yatabe-Machi, Tsukuba-Gun, Ibaragi-Ken 305, Japan and were accorded the FERM BP numbers indicated above.

The invention now being generally described, the same will be better understood by reference to certain specific examples which are included herein for purposes of illustration only and are not intended to be limiting of the invention or any embodiment thereof, unless specified.

EXAMPLE 1

After being adjusted to a pH of 7.0, 20 ml of culture medium (separately sterilized) containing 10 g/dl of glucose, 4 g/dl of ammonium sulfate, 0.1 g/dl of $KH_2PO_4$, 0.1 g/dl of $MgSO_4.7H_2O$, 0.1 mg/dl of $FeSO_4.7H_2O$, 0.1 mg/dl of $MnSO_4.4H_2O$, 100 µg/l of biotin, 100 µgl of thiamine hydrochloride, 80 mg-N/dl of acid hydrolysate of soybean proteins and 5 g/dl of calcium carbonate was placed in a 50 ml shouldered flask and then sterilized by mens of heating. One platinum loopful each of the strains shown in Table 2 was inoculated in the medium and then cultured therein with shaking for 4 days, and the temperature of the medium was maintained at 31.5° C. In each of the culture media, L-threonine was accumulated in quantities shown on Table 3. AJ 12312 was cultured in the same manner as above to give 1 liter of culture broth, and the cells were removed therefrom by centrifugation. The supernatant was passed through Dia-Ion SK-B (strongly acidic ion exchange resin). The resin was washed with water and eluted with 2N aqueous ammonia. The eluent was then condensed to give 6.2 g of crystals of L-threonine.

TABLE 2

| Strain | Characteristics | Quantity of L-threonine Accumulated (g/l) |
|---|---|---|
| ATCC 21269 | AHV$^r$ | 9.3 |
| AJ 12312 FERM BP-1173 | AHV$^r$, MPA$^r$ | 12.5 |
| AJ 12313 | AHV$^r$, Ile$^-$ | 14.0 |
| AJ 12314 | AHV$^r$, Ile$^-$, MPA$^r$ | 16.2 |
| AJ 12315 | AHV$^r$ | 8.6 |
| AJ 12316 | AHV$^r$, MPA$^r$ | 12.0 |
| AJ 12317 | AHV$^r$, Ile$^-$ | 13.0 |
| AJ 12318 FERM BP-1172 | AHV$^r$, Ile$^-$, MPA$^r$ | 15.0 |

AHV$^r$: Resistant to AHV
MPA$^r$: Resistant to MPA
Ile$^-$: Requiring isoleucine

EXAMPLE 2

After being adjusted to a pH of 7.0, 50 ml of sead medium containing 5 g/dl of glucose, 0.2 g/dl of ammonium sulfate, 0.2 g/dl of urea, 0.15 g/dl of $KH_2PO_4$, 0.04 g/dl of $MgSO_4.7H_2O$, 100 μg/l of thiamine hydrochloride, 300 μg/l of biotin, 140 mg/dl (as total nitrogen) of acid hydrolysate of soybean proteins, was placed in a 500 ml of Sakaguchi flask and then sterilized by means of heating.

One platinum loopful each of the strains shown in Table 3 was inoculated in the medium and then cultured therein with shaking for 18 hours, and the temperature of the medium was maintained at 31.5° C.

On the other hand, after being adjusted to a pH of 7.0, 285 ml of culture medium containing 2 g/dl of glucose, 1 g/dl of ammonium sulfate, 0.15 g/dl of $KH_2PO_4$, 0.04 g/dl of $MgSO_4.7H_2O$, 1 mg/dl of $FeSO_4.7H_2O$, 1 mg/dl of $MnSO_4.7H_2O$, 50 μg/l of biotin, 500 μg/l of thiamine hydrochloride, 32 mg/dl (as total nitrogen) of acid hydrolysate of soybean proteins and 40 mg of L-isoleucine was placed in a 1000 ml fermenter and then sterilized by means of heating. 15 ml of each sead culture broth was inoculated in the medium.

A solution mixture comprising a molar ratio of acetate to ammonium acetate of 1:0.2 was fed into the culture medium and the culture medium was maintained at pH 7.5 under aerobic culture conditions for 3 days. Accumulation of L-threonine and yield of acetate (weight) are were shown in Table 3.

TABLE 3

| Strain | Characteristics | L-threonine accumulated | yield of acetate (%) |
|---|---|---|---|
| ATCC 21269 | $AHV^r$ | 15.0 | 11.0 |
| AJ 12312 FERM BP-1173 | $AHV^r$, $MPA^r$ | 21.0 | 14.0 |
| AJ 12313 | $AHV^r$, $Ile^-$ | 21.5 | 14.3 |
| AJ 12314 | $AHV^r$, $Ile^-$, $MPA^r$ | 25.0 | 17.2 |

Many modifications and variations of the present invention are possible in light of the above teachings. Therefore, it is to be understood that within the scope of the appended claims, the invention may be practiced otherwise than as specifically described.

What is claimed as new and desired to be secured by Letters Patent of the United States is:

1. A method for producing L-threonine by fermentation which comprises:

culturing a microorganism selected from the group consisting of *Corynebacterium acetoacidophilum* FERM BP-1172 and *Brevibacterium flavum* FERM BP-1173 in an aqueous nutrient medium containing assimilable sources of carbon, nitrogen, and inorganic substances;

accumulating L-threonine in the medium, and then recovering the L-threonine accumulated therein.

* * * * *